US009565876B2

(12) United States Patent
Tsai

(10) Patent No.: US 9,565,876 B2
(45) Date of Patent: Feb. 14, 2017

(54) ATOMIZER

(71) Applicant: Wei Li Tsai, Port Moody (CA)

(72) Inventor: Wei Li Tsai, Port Moody (CA)

( * ) Notice: Subject to any disclaimer, the term of this patent is extended or adjusted under 35 U.S.C. 154(b) by 390 days.

(21) Appl. No.: 14/246,436

(22) Filed: Apr. 7, 2014

(65) Prior Publication Data

US 2015/0208725 A1 Jul. 30, 2015

(30) Foreign Application Priority Data

Jan. 28, 2014 (TW) ............................. 103201833 U

(51) Int. Cl.

| | |
|---|---|
| ***A61M 16/00*** | (2006.01) |
| ***F24F 3/14*** | (2006.01) |
| ***A24F 47/00*** | (2006.01) |
| ***H05B 1/02*** | (2006.01) |

(52) U.S. Cl.

CPC ........... *A24F 47/008* (2013.01); *H05B 1/0244* (2013.01)

(58) Field of Classification Search

None

See application file for complete search history.

(56) References Cited

U.S. PATENT DOCUMENTS

| | | | | |
|---|---|---|---|---|
| 4,547,656 A * | 10/1985 | Swiatosz | F41H 9/06 | 392/397 |
| 4,764,660 A * | 8/1988 | Swiatosz | F41H 9/06 | 219/505 |
| 4,818,843 A * | 4/1989 | Swiatosz | A62B 27/00 | 392/397 |
| 5,957,382 A * | 9/1999 | Thomas | F41H 9/06 | 239/135 |
| 6,477,890 B1 * | 11/2002 | Hulsebus | F41H 9/06 | 239/136 |
| 6,584,971 B1 * | 7/2003 | Denyer | A61M 15/00 | 128/203.12 |
| 8,737,826 B2 * | 5/2014 | Stauffer | A63J 5/025 | 239/136 |
| 8,781,306 B2 * | 7/2014 | Hatten | A61M 11/041 | 128/203.27 |
| 8,917,980 B2 * | 12/2014 | Scully | A63J 5/025 | 392/397 |
| 2002/0071664 A1 * | 6/2002 | Aronie | A63H 33/28 | 392/399 |
| 2002/0114622 A1 * | 8/2002 | Aronie | A63H 33/28 | 392/399 |
| 2012/0269497 A1 * | 10/2012 | Hatten | A61M 11/041 | 392/386 |
| 2014/0041658 A1 * | 2/2014 | Goodman | F22B 1/282 | 128/203.14 |

(Continued)

FOREIGN PATENT DOCUMENTS

| | | |
|---|---|---|
| CN | 200983833 Y | 12/2007 |
| CN | 202621366 U | 12/2012 |

*Primary Examiner* — Thor Campbell

(74) *Attorney, Agent, or Firm* — Rosenberg, Klein & Lee

(57) ABSTRACT

An atomizer is disclosed. The atomizer of the present invention comprises a main unit, a pipe, and a vaporizer. The vaporizer of the present invention comprises a pneumatic switch which is triggered by the airflow from the main unit. There is no conducting wire between the main unit and the vaporizer. The length of the pipe is determined according to the requirement of the user. In one embodiment of the present invention, the atomizer is remote controllable.

19 Claims, 4 Drawing Sheets

(56) References Cited

U.S. PATENT DOCUMENTS

| | | | | |
|---|---|---|---|---|
| 2014/0069424 | A1* | 3/2014 | Poston | A24F 47/008<br>128/202.21 |
| 2014/0096781 | A1* | 4/2014 | Sears | A24F 47/008<br>131/328 |
| 2014/0096782 | A1* | 4/2014 | Ampolini | A24F 47/008<br>131/328 |
| 2014/0261486 | A1* | 9/2014 | Potter | A24F 47/008<br>131/328 |
| 2014/0345635 | A1* | 11/2014 | Rabinowitz | A24B 15/16<br>131/352 |
| 2014/0346689 | A1* | 11/2014 | Dubief | A24F 47/008<br>261/142 |
| 2015/0272225 | A1* | 10/2015 | Worm | A24F 47/008<br>131/328 |
| 2016/0021931 | A1* | 1/2016 | Hawes | A24F 47/008<br>131/328 |
| 2016/0120229 | A1* | 5/2016 | Tucker | H01C 17/00<br>131/329 |
| 2016/0143361 | A1* | 5/2016 | Juster | A24F 47/008<br>392/404 |

* cited by examiner

30

ATOMIZER

FIELD OF THE INVENTION

The present invention relates to an atomizer, and more particularly to an atomizer wherein the length of the pipe between the main unit and the vaporizer is adjustable.

BACKGROUND OF THE INVENTION

Nowadays, the atomizer of the prior art comprises a conducting wire between the main unit and the vaporizer for power and control signal transmission. In the limitation of the prior art, the length of the pipe and the conducting wire between the main unit and the vaporizer of the atomizer is determined when the product is produced. It is not adjustable for users.

For long conducting wire and pipe, the cost of material is high. It is troublesome for user to arrange or hide the wire and pipe when using the atomizer. For short conducting wire and pipe, the configuration for locating the main unit and the vaporizer is limited. Furthermore, due to the user's habit and physique, different length of the wire and pipe is needed.

In the prior art, the atomizer can only be operated by a single user. The patterns of application and performance are limited.

SUMMARY OF THE PRESENT INVENTION

It is an objective of the present invention to provide an atomizer, and more particularly an atomizer wherein the length of the pipe between the main unit and the vaporizer is adjustable.

It is another objective of the present invention to provide an atomizer without conducting wire between the main unit and the vaporizer.

It is still another objective of the present invention to provide an atomizer which is remote controllable.

The present invention provides an atomizer, comprising: a main unit having a main circuit, a battery, and an inflator pump; a pipe having a first end and a second end, wherein the first end of the pipe is connected to the inflator pump; and a vaporizer connected to the second end of the pipe, wherein the vaporizer comprises a control circuit, a battery, a pneumatic switch, a heater, and a cartridge; wherein the main circuit comprises a start switch, after triggering the start switch, the main circuit drives the inflator pump to work and produce airflow, the airflow flows through the pipe and triggers the pneumatic switch, the control circuit controls the heater to heat the cartridge and produce smoke, and then the smoke flows out with the airflow.

In one embodiment of the present invention, the atomizer further comprises a remote controller for controlling the main circuit remotely.

In one embodiment of the present invention, the remote controller comprises a remote control circuit having a start switch and a wireless transmitter, the main circuit comprises a wireless receiver; when the start switch of the remote control circuit is triggered, the wireless transmitter transmits a start signal to the wireless receiver of the main circuit.

In one embodiment of the present invention, the main unit comprises: a case for containing the elements of the main unit; and a cap disposed movably on the case, wherein the start switch of the main circuit is triggered by pressing the cap.

In one embodiment of the present invention, the case and the cap are assembled by one or more sets of joint holes and joint pins disposed on the case and the cap respectively.

In one embodiment of the present invention, the vaporizer further comprises: a handle shell for containing the battery, control circuit, and pneumatic switch, wherein one end of the handle shell is connected to the pipe, the other end of the handle shell is connected to the heater; and a cartridge shell connected to the heater for containing the cartridge.

In one embodiment of the present invention, the main circuit and the remote control circuit comprise a pairing button respectively for pairing the remote controller and the main unit.

In one embodiment of the present invention, the main circuit further comprises a function switch for switching the main unit to a power off status, a main circuit control only status, or a remote controllable status.

In one embodiment of the present invention, the main circuit and the vaporizer comprise an LED respectively for displaying status.

In one embodiment of the present invention, the pipe has a length determined by the requirement of user.

In one embodiment of the present invention, the atomizer further comprises two connectors disposed at the two ends of the pipe to facilitate to connect with the main unit and the vaporizer.

In one embodiment of the present invention, the pneumatic switch is embodied by a pressure valve.

In one embodiment of the present invention, the main unit further comprises one or more springs to support the cap.

In one embodiment of the present invention, the cartridge contains nicotine liquid.

In one embodiment of the present invention, the remote controller further comprises: a case for containing the elements of the remote controller; and a cap disposed movable on the case, wherein the start switch of the remote control circuit is triggered by pressing the cap of the remote controller.

In one embodiment of the present invention, the case and the cap of the remote controller are assembled by one or more sets of joint holes and joint pins disposed on the case and the cap of the remote controller respectively.

In one embodiment of the present invention, the remote controller further comprises one or more springs to support the cap of the remote controller.

In one embodiment of the present invention, the main circuit further comprises a power socket for charging the battery of the main unit.

In one embodiment of the present invention, the remote control circuit further comprises a power socket for charging the battery of the remote controller.

In one embodiment of the present invention, the remote control circuit further comprises an LED for displaying status.

DETAILED DESCRIPTION OF THE PREFERRED EMBODIMENTS

Figure 1:
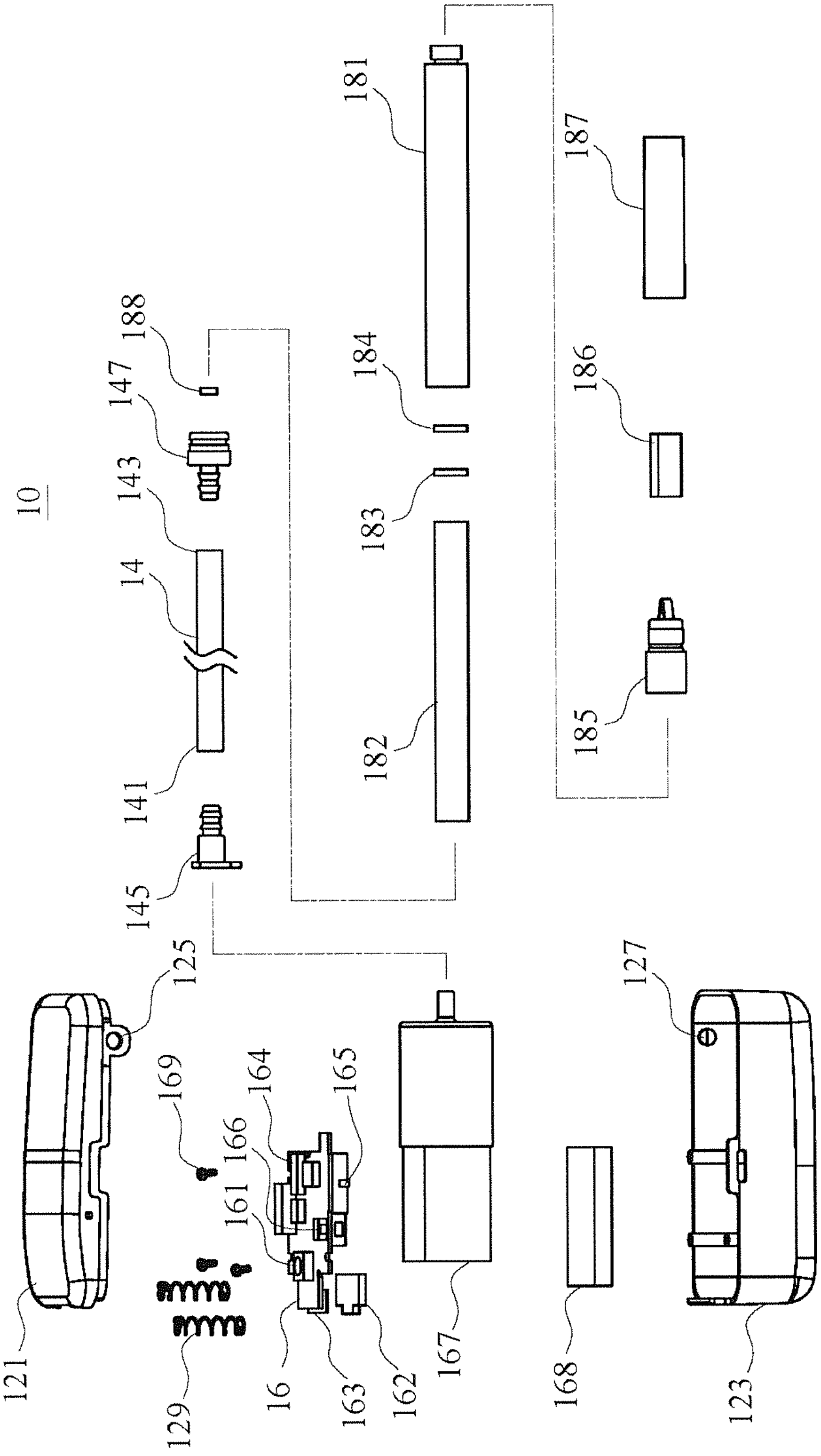
FIG. 1 is a schematic explosion diagram of an atomizer in accordance with one embodiment of the present invention.
Figure 2:
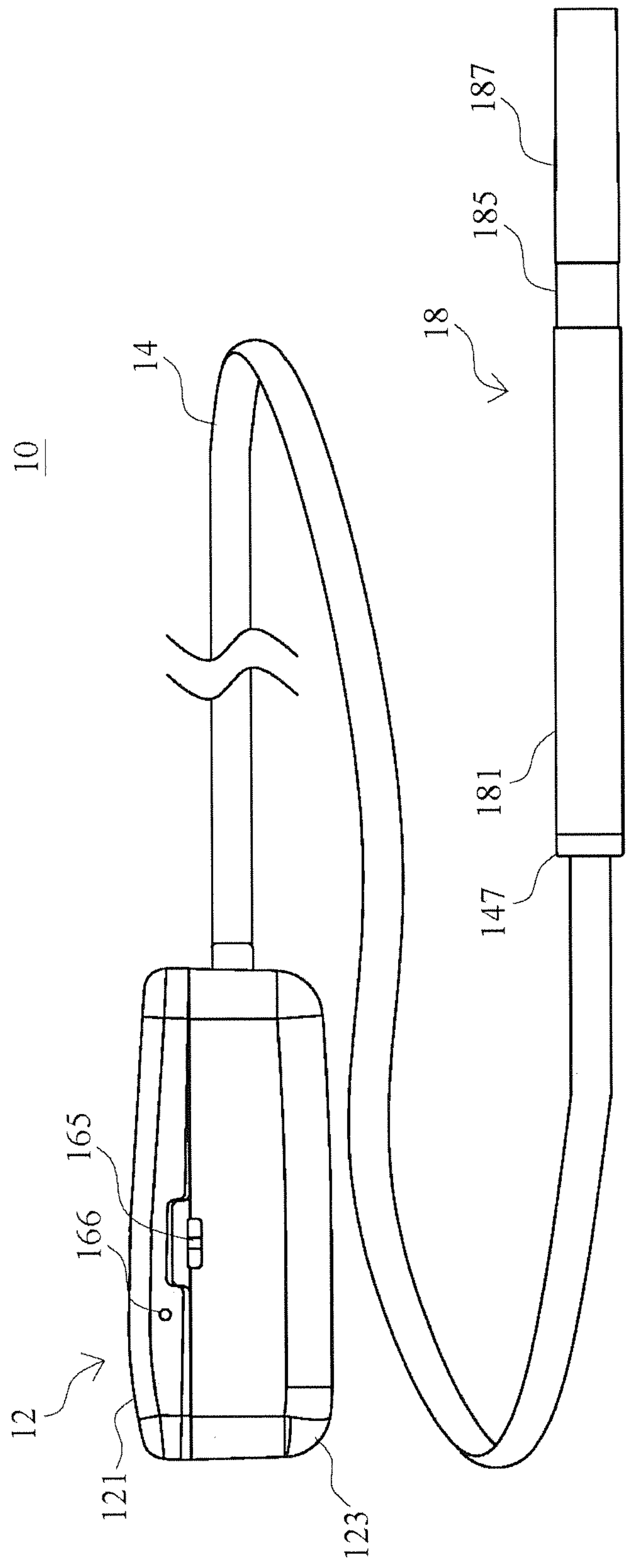
FIG. 2 is a schematic assembly diagram of the atomizer in accordance with the embodiment shown in FIG. 1.

Referring to FIG. 1 and FIG. 2, a schematic explosion diagram and a schematic assembly diagram of the atomizer in accordance with one embodiment of the present invention are illustrated. In the present embodiment, the atomizer 10 comprises a main unit 12, a pipe 14 and a vaporizer 18. The main unit 12 comprises a main circuit 16, a battery 168, and an inflator pump 167. The pipe 14 having a first end 141 and a second end 143. The first end 141 and the second end 143 of the pipe 14 are connected to the inflator pump 167 and the vaporizer 18 respectively. The vaporizer 18 comprises a battery 182, a control circuit 183, a pneumatic switch 184, a heater 185, and a cartridge 186.

A start switch 161 is disposed in the main circuit 16. When a user triggers the start switch 161, the main circuit 16 drives the inflator pump 167 to work and produce airflow. The airflow is transmitted to the vaporizer 18 through the pipe 14 and triggers the pneumatic switch 184. The control circuit 183 of the vaporizer 18 controls the heater 185 to heat the cartridge 186 for producing smoke. The smoke flows out with the airflow and performs according to the action of the user.

In one embodiment of the present invention, the main unit 12 comprises a case 123 and a cap 121. The components of the main unit 12 are disposed in the case 123. The cap 121 is movably disposed on the case 123. Users can press the cap 121 to trigger the start switch 161.

In one embodiment of the present invention, the case 123 and the cap 121 are assembled by one or more sets of joint holes 125 and joint pins 127. Furthermore, one or more springs 129 are disposed in the main unit 12 for the cap 121 to restore after been compressed.

In one embodiment of the present invention, the vaporizer 18 comprises a handle shell 181 and a cartridge shell 187. The battery 182, the control circuit 183, and the pneumatic switch 184 are disposed inside the handle shell 181. One end of the handle shell 181 is connected to the pipe 14, the other end of the handle shell 181 is connected to the heater 185. The cartridge shell 187 is used for containing the cartridge 186 and is connected to the heater 185.

In one embodiment of the present invention, the main circuit 16 further comprises an LED 162 for displaying the status of the main unit 12. The vaporizer 18 further comprises an LED 188 for displaying the status of the vaporizer 18.

In one embodiment of the present invention, the atomizer 10 further comprises two connectors 145, 147 disposed at the two ends 141, 143 of the pipe 14 to facilitate to connect with the main unit 12 and the vaporizer 18 respectively. Furthermore, the connector 147 is transparent for user to observe the LED 188 signal.

In one embodiment of the present invention, the pneumatic switch 184 is embodied by a pressure valve. When the air pressure is higher than a predetermined value, the pneumatic switch 184 will be triggered and enable the control circuit 183.

In one embodiment of the present invention, the length of the pipe 14 is determined by the requirement of the user. Since there is no conducting wire between the main unit 12 and the vaporizer 18, users can cut the pipe 14 with proper length according to various requirements.

In one embodiment of the present invention, the main circuit 16 comprises a power socket 163 for charging the battery 168.

In one embodiment of the present invention, the cartridge 186 contains nicotine liquid.

Figure 3:
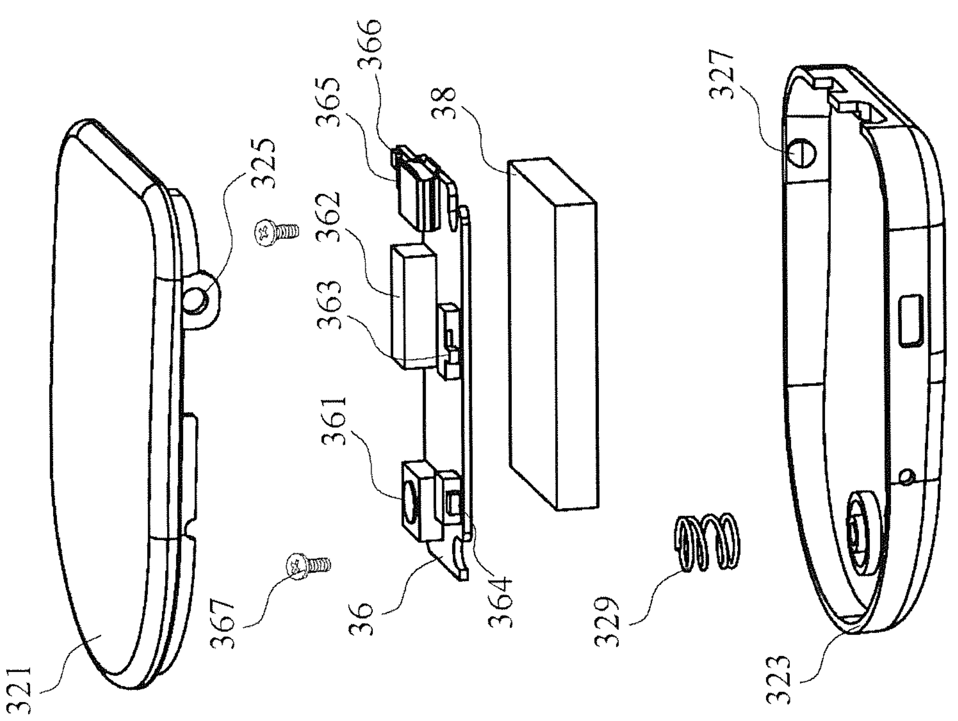
FIG. 3 is a schematic explosion diagram of the remote controller in accordance with one embodiment of the present invention.
Figure 4:
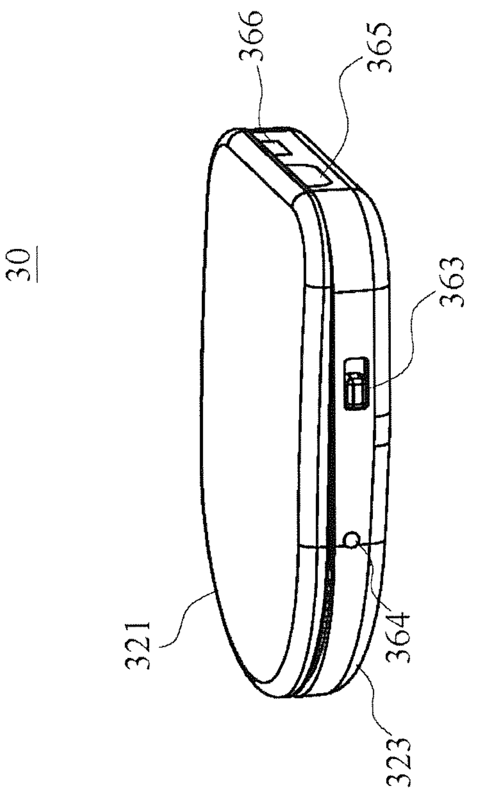
FIG. 4 is schematic assembly diagram of the remote controller in accordance with the embodiment shown in FIG. 3.

Referring to FIGS. 1, 3, and 4, a schematic explosion diagram of the atomizer, a schematic explosion diagram and a schematic assembly diagram of the remote controller in accordance with one embodiment of the present invention are illustrated. In one embodiment of the present invention, the atomizer 10 further comprises a remote controller 30 for controlling the main circuit 16 remotely.

In one embodiment of the present invention, the remote controller 30 comprises a remote control circuit 36. The remote control circuit 36 comprises a start switch 361 and a wireless transmitter 362. The main circuit 16 further comprises a wireless receiver 164. When the start switch 361 of the remote controller 30 is triggered, the wireless transmitter 362 transmits a start signal to the main circuit 16. Once the wireless receiver 164 receives the start signal, the main circuit 16 drives the inflator pump 167 to operate.

In one embodiment of the present invention, pairing buttons 166, 364 are disposed in the main circuit 16 and the remote control circuit 36 respectively. The main unit 12 works in a pairing status after the pairing button 166 is pressed. If the pairing button 364 of the remote controller 30 is also pressed during a predetermined period, the main unit 12 and the remote controller 30 will be paired. And then, the signal transmission between the main unit 12 and the remote controller 30 will be more reliable and free from interference. In one embodiment of the present invention, the remote controller 30 can be paired with a plurality of main units 12 for variety of performances.

In one embodiment of the present invention, the main circuit 16 further comprises a function switch 165 for switching the main unit 12 to power off status, main circuit control only status, or remote controllable status.

In one embodiment of the present invention, the remote controller 30 further comprises a case 323 and a cap 321. The components of the remote controller 30 are disposed in the case 323. The cap 321 is movably disposed on the case 323. Users can press the cap 321 to trigger the start switch 361.

In one embodiment of the present invention, the case 323 and the cap 321 are assembled by one or more sets of joint hole 325 and joint pin 327. Furthermore, one or more springs 329 are disposed in the remote controller 30 for the cap 321 to restore after been compressed.

In one embodiment of the present invention, the remote control circuit 36 comprises a power socket 365 for charging the battery 38.

In one embodiment of the present invention, the remote control circuit 36 further comprises an LED 366 for displaying the status of the remote controller 30.

In one embodiment of the present invention, the main circuit 16 is fixed to the case 123 by one or more screws 169.

In one embodiment of the present invention, the remote control circuit 36 is fixed to the case 323 by one or more screws 367.

By using the atomizer 10 of the present invention, users can cut the pipe 14 with proper length according to various requirements. It is more convenient for users to arrange of hide the pipe 14 when using the atomizer 10. Furthermore, the atomizer 10 of the present invention is remote controllable, and the remote controller 30 can be paired with a plurality of main units 12. This provides the variety of performances for the atomizer 10 of the present invention.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. An atomizer, comprising:

a main unit having a main circuit, a battery, and an inflator pump;

a pipe having a first end and a second end, wherein the first end of the pipe is connected to the inflator pump; and a vaporizer connected to the second end of the pipe, wherein the vaporizer comprises a control circuit, a battery, a pneumatic switch, a heater, and a cartridge;

wherein the main circuit comprises a start switch, after triggering the start switch, the main circuit drives the inflator pump to work and produce airflow, the airflow flows through the pipe and triggers the pneumatic switch, the control circuit controls the heater to heat the cartridge and produce smoke, and then the smoke flows out with the airflow;

wherein the main unit comprises:

a case for containing the elements of the main unit; and a cap disposed movably on the case, wherein the start switch of the main circuit is triggered by pressing the cap.

2. The atomizer as claimed in claim 1, further comprising a remote controller for controlling the main circuit remotely.

3. The atomizer as claimed in claim 2, wherein the remote controller comprises a remote control circuit having a start switch and a wireless transmitter, the main circuit comprises a wireless receiver; when the start switch of the remote control circuit is triggered, the wireless transmitter transmits a start signal to the wireless receiver of the main circuit.

4. The atomizer as claimed in claim 1, wherein the case and the cap are assembled by one or more sets of joint holes and joint pins disposed on the case and the cap respectively.

5. The atomizer as claimed in claim 1, wherein the vaporizer further comprises:

a handle shell for containing the battery, control circuit, and pneumatic switch, wherein one end of the handle shell is connected to the pipe, the other end of the handle shell is connected to the heater; and a cartridge shell connected to the heater for containing the cartridge.

6. The atomizer as claimed in claim 3, wherein main circuit and the remote control circuit comprise a pairing button respectively for pairing the remote controller and the main unit.

7. The atomizer as claimed in claim 3, wherein the main circuit further comprises a function switch for switching the main unit to a power off status, a main circuit control only status, or a remote controllable status.

8. The atomizer as claimed in claim 1, wherein the main circuit and the vaporizer comprises an LED respectively for displaying status.

9. The atomizer as claimed in claim 1, wherein the pipe has a length determined by the requirement of user.

10. The atomizer as claimed in claim 1, further comprising two connectors disposed at the two ends of the pipe to facilitate to connect with the main unit and the vaporizer.

11. The atomizer as claimed in claim 1, wherein the pneumatic switch is embodied by a pressure valve.

12. The atomizer system as claimed in claim 4, wherein the main unit further comprises one or more springs to support the cap.

13. The atomizer as claimed in claim 1, wherein the cartridge contains nicotine liquid.

14. The atomizer as claimed in claim 3, wherein the remote controller further comprises:

a case for containing the elements of the remote controller; and a cap disposed movable on the case, wherein the start switch of the remote control circuit is triggered by pressing the cap of the remote controller.

15. The atomizer as claimed in claim 14, wherein the case and the cap of the remote controller are assembled by one or more sets of joint holes and joint pins disposed on the case and the cap of the remote controller respectively.

16. The atomizer as claimed in claim 15, wherein the remote controller further comprises one or more springs to support the cap of the remote controller.

17. The atomizer as claimed in claim 1, wherein the main circuit further comprises a power socket for charging the battery of the main unit.

18. The atomizer as claimed in claim 3, wherein the remote control circuit further comprises a power socket for charging the battery of the remote controller.

19. The atomizer as claimed in claim 3, wherein the remote control circuit further comprises an LED for displaying status.

* * * * *